United States Patent
Diehl et al.

(10) Patent No.: US 9,206,094 B2
(45) Date of Patent: Dec. 8, 2015

(54) PROCESS FOR SELECTIVELY HYDROGENATING A GASOLINE CUT IN THE PRESENCE OF A SUPPORTED SULPHIDE CATALYST PREPARED USING AT LEAST ONE CYCLIC OLIGOSACCHARIDE

(75) Inventors: Fabrice Diehl, Lyons (FR); Elodie Devers, Lyons (FR)

(73) Assignee: IFP ENERGIES NOUVELLES, Rueil Malmaison (FR)

( * ) Notice: Subject to any disclaimer, the term of this patent is extended or adjusted under 35 U.S.C. 154(b) by 493 days.

(21) Appl. No.: 13/813,021

(22) PCT Filed: Jun. 24, 2011

(86) PCT No.: PCT/FR2011/000367
§ 371 (c)(1),
(2), (4) Date: Apr. 4, 2013

(87) PCT Pub. No.: WO2012/022849
PCT Pub. Date: Feb. 23, 2012

(65) Prior Publication Data
US 2013/0211163 A1 Aug. 15, 2013

(30) Foreign Application Priority Data
Jul. 29, 2010 (FR) ..................................... 10 03190

(51) Int. Cl.
| | |
|---|---|
| *C07C 5/05* | (2006.01) |
| *B01J 23/652* | (2006.01) |
| *B01J 23/85* | (2006.01) |
| *B01J 23/881* | (2006.01) |
| *B01J 23/882* | (2006.01) |
| *B01J 23/883* | (2006.01) |
| *B01J 23/888* | (2006.01) |
| *B01J 35/10* | (2006.01) |
| *B01J 37/02* | (2006.01) |
| *B01J 37/20* | (2006.01) |
| *C10G 45/38* | (2006.01) |
| *C10G 45/32* | (2006.01) |
| *C10G 45/34* | (2006.01) |
| *B01J 23/70* | (2006.01) |
| *B01J 23/75* | (2006.01) |
| *B01J 23/755* | (2006.01) |
| *C07C 5/02* | (2006.01) |

(52) U.S. Cl.
CPC ................. *C07C 5/05* (2013.01); *B01J 23/652* (2013.01); *B01J 23/85* (2013.01); *B01J 23/881* (2013.01); *B01J 23/882* (2013.01); *B01J 23/883* (2013.01); *B01J 23/888* (2013.01); *B01J 35/1014* (2013.01); *B01J 35/1019* (2013.01); *B01J 35/1038* (2013.01); *B01J 35/1042* (2013.01); *B01J 35/1047* (2013.01); *B01J 37/0201* (2013.01); *B01J 37/0203* (2013.01); *B01J 37/20* (2013.01); *C10G 45/38* (2013.01); *C10G 2300/104* (2013.01); *C10G 2300/1044* (2013.01); *C10G 2300/202* (2013.01); *C10G 2300/301* (2013.01); *C10G 2300/4018* (2013.01)

(58) Field of Classification Search
CPC ........ C10G 45/32; C10G 45/34; C10G 45/36; B01J 23/70; B01J 23/75; B01J 23/755; C07C 5/00; C07C 5/02
See application file for complete search history.

(56) References Cited

U.S. PATENT DOCUMENTS

| | | | |
|---|---|---|---|
| 6,280,610 B1 | 8/2001 | Uragami et al. | |
| 7,745,372 B2 | 6/2010 | Li et al. | |
| 2005/0137434 A1 | 6/2005 | Li et al. | |
| 2012/0093703 A1* | 4/2012 | Lewis et al. | ................. 423/213.2 |

FOREIGN PATENT DOCUMENTS

| | | |
|---|---|---|
| FR | 2864102 A1 | 6/2005 |
| WO | WO 9641848 | 12/1996 |

OTHER PUBLICATIONS

Jong-Tae Lee and Howard Alper: Regioselective Hydrogenation of Conjugated Dienes Catalyzed by Hydridopentacyanocobaltate Anion Using B-Cyclodextrin as the Phase-Transfer Agent and Lanthanide halides as Promoters:, J. Org. Chem, vol. 55, pp. 1854-1856; Dec. 31, 1990, XP002628319.
International Search Report for PCT/FR2011/000367, Date of the actual completion of the international search: Jan. 11, 2012, Date of the mailing of the international search report: Jan. 23, 2012.

\* cited by examiner

*Primary Examiner* — Brian McCaig
(74) *Attorney, Agent, or Firm* — Millen, White, Zelano and Branigan, P.C.

(57) ABSTRACT

Selective hydrogenation of a gasoline cut containing polyunsaturated hydrocarbons containing at least 2 carbon atoms per molecule and having an end point of 250° C. or less, by bringing said gasoline cut into contact with at least one catalyst the active phase of which comprises at least one metal from group VIII and at least one metal from group VIB deposited on a support.

12 Claims, No Drawings

PROCESS FOR SELECTIVELY HYDROGENATING A GASOLINE CUT IN THE PRESENCE OF A SUPPORTED SULPHIDE CATALYST PREPARED USING AT LEAST ONE CYCLIC OLIGOSACCHARIDE

FIELD OF THE INVENTION

The present invention relates to the field of the hydrotreatment of gasoline cuts, in particular gasoline cuts derived from fluidized bed catalytic cracking units (FCC). Hydrotreatment (HDT) is a general term employed to designate the series of processes for eliminating polyunsaturated compounds, in particular diolefins (hydrogenation), as well as for eliminating organic compounds containing heteroatoms, in particular sulphur (hydrodesulphurization, HDS), the presence of said compounds being undesirable in gasolines which have to satisfy ever more severe automobile pollution regulations. More precisely, the present invention relates to a process for the selective hydrogenation of a gasoline cut, principally a gasoline cut derived from a fluidized bed catalytic cracking unit, containing organic sulphur-containing compounds, especially diolefins. The quantity of polyunsaturated compounds, especially diolefins, as well as that of sulphur have to be reduced in order to be able to upgrade said gasoline cut in the gasoline pool once it has been hydrotreated. The selective hydrogenation process of the invention means that light sulphur-containing compounds generally containing 1 to 3 carbon atoms per molecule can be eliminated by making said compounds heavier without affecting the heavier sulphur-containing compounds also present in the gasoline cut to be treated, said heavier sulphur-containing compounds being able to be transformed into $H_2S$ during a subsequent hydrodesulphurization step.

In order to provide better global positioning of the selective hydrogenation process of the invention, the selective hydrogenation process of the invention can advantageously be integrated into a facility in which the reaction unit carrying out said selective hydrogenation process is placed upstream of a separation column that can produce a first stream formed by a light gasoline cut, hydrogenated and substantially depleted in sulphur, with a good octane number and which can be added directly to the gasoline pool, and a second stream formed by a highly sulphur-enriched heavy gasoline cut which is subsequently treated in a hydrodesulphurization unit in order to obtain a gasoline that can also be added directly to the gasoline pool.

PRIOR ART

The increasing severity of automobile pollution regulations in 2009 in the European Community is forcing refiners to reduce the sulphur content in gasolines very substantially to a maximum of 10 parts per million (ppm) of sulphur from the 1 Jan. 2009, down from 50 ppm on 1 Jan. 2005 (measured using the ASTM D-4294 method). Further, these new regulations are also accompanied by restrictions regarding the octane number.

Conversion gasolines, and more particularly those from fluidized bed catalytic cracking (FCC gasoline), have high mono-olefin and sulphur contents and may represent 30% to 50% by volume of the gasoline pool. Almost 90% of the sulphur present in the gasolines can thus be attributed to gasolines derived from fluidized bed catalytic cracking processes.

Gasoline cuts, and more particularly gasolines derived from FCC, contain a large proportion of unsaturated compounds in the form of mono-olefins (approximately 20% to 50% by weight) and diolefins (0.5% to 5% by weight). Diolefins are unstable compounds which tend to form gums by polymerization; as a consequence, they generally have to be eliminated by hydrogenation before any treatment of such gasolines is carried out, in particular hydrodesulphurization (HDS) treatments intended to bring the sulphur contents of the gasolines to specification. However, it is essential that the hydrogenation be applied selectively to the diolefins in order to limit hydrogenation of the mono-olefins, which would result in a loss of octane number and limit the hydrogen consumption. Further, the gasoline cuts and more particularly the gasolines derived from FCC, contain a non-negligible proportion of sulphur in the form of organic sulphur-containing compounds (200 ppm at 0.5% by weight), which has to be eliminated in order to upgrade said gasoline cuts to satisfy current regulations in terms of automobile pollution standards. Said organic sulphur-containing compounds are partly formed from light saturated sulphur-containing compounds with a boiling point which is lower than the boiling point of thiophene, which has a boiling point of 84° C., such as methanethiol, ethanethiol or dimethylsulphide. The elimination of such light sulphur-containing compounds by converting said compounds into heavier sulphur-containing compounds with a higher molecular mass which can be eliminated in a subsequent hydrodesulphurization step has already been proposed (EP 1.077 247 A1).

Better quality gasolines that satisfy environmental requirements are always being researched; to this end, catalytic formulations and processes that can selectively hydrogenate diolefins to mono-olefins and/or transform light sulphur-containing compounds such as mercaptans by converting them into heavier compounds have already been described. As an example, European patent EP 0 685 552 B1 proposes a process for the hydrogenation of diolefins and for reducing the quantity of mercaptans contained in a catalytically cracked gasoline based on a catalyst containing in the range 0.1% to 1% by weight of palladium deposited on an alumina-based support. However, the catalytic performances of such prior art catalysts is not entirely satisfactory, especially in terms of activity.

An effective means for increasing the activity of supported catalysts is to increase the quantity of active phase in the sulphide form, which initially results in maximized deposition of the active phase in the oxide form associated with the surface area of the support. However, this maximized quantity (normally deposited by dry impregnation) is limited by the textural properties of the support, in particular its specific surface area and its pore volume. Furthermore, in the particular case in which the support used comprises the element aluminium, this large concentration of deposited oxide phase favours the formation of crystalline oxide phases of the $Al_2(MoO_4)_3$, $CoAl_2O_4$ or $NiAl_2O_4$ type, etc, which prove to be refractory to the sulphurization step. This logically results in an indirect loss of catalytic activity since not all of the deposited oxide phase is used to its maximum potential. Furthermore, an increase in the active phase content may result in the formation of crystallites of $MoO_3$, NiO, CoO, $Co_3O_4$ or $CoMoO_4$, of a size sufficiently large to be detected in X ray diffraction. These species are also known to reduce the degree of sulphurization of hydrotreatment catalysts and thus their performances.

The composition and use of hydrotreatment/hydrogenation catalysts have been described particularly well in the article by B S Clausen, H T Topsøe, F E Massoth in the publication "Catalysis Science and Technology", 1996, volume 11, Springer-Verlag. Thus, these catalysts generally comprise at least one metal from group VIB and/or at least one metal from group VIII of the periodic classification of the elements. The most common formulations are of the cobalt-molybdenum (CoMo), nickel-molybdenum (NiMo) and nickel-tungsten (NiW) type. These catalysts may be in the bulk or in the supported form. In this latter case, the porous matrix is generally an amorphous or low crystallinity oxide (alumina, silica-alumina, etc), optionally associated with a zeolitic or non-zeolitic molecular sieve. After preparation, said catalysts are usually in the oxide form. Their active and stable form for hydrotreatment processes, in particular for hydrogenation processes, is the sulphurized form, and so these catalysts undergo a sulphurization step.

However, the dispersion of the active phase or of said oxide or oxyhydroxide precursors is directly linked to the specific surface area of the support: for high surface densities of molybdenum, the formation of phases which are refractory to sulphurization by sintering has been reported. Novel techniques for the preparation of catalysts have to be developed in order to further improve the performances of said catalysts and comply with future legislation.

In particular, interactions between the support and the precursors for the active phase which result in species which are refractory to sulphurization (for example, $Al_2(MoO_4)_3$, $CoAl_2O_4$ or $NiAl_2O_4$, which are of no use to the catalytic reaction and have undesirable effects on the catalytic activity, should be controlled.

The present invention proposes the development of a novel process for the selective hydrogenation of gasoline cuts, particular gasoline cuts derived from FCC, containing saturated light sulphur-containing compounds and polyunsaturated compounds, especially diolefins, in the presence of a supported catalyst which is prepared in the presence of an organic compound formed from at least one cyclic oligosaccharide in a manner which results in improved catalytic performances, in particular in terms of activity.

SUMMARY AND IMPORTANCE OF THE INVENTION

The present invention concerns a process for the selective hydrogenation of a gasoline cut containing polyunsaturated hydrocarbons containing at least 2 carbon atoms per molecule and having an end point of 250° C. or less, said cut having a polyunsaturated hydrocarbons content in the range 0.5% to 5% by weight and a sulphur content in the range 200 to 5000 ppm by weight, said process consisting of bringing said gasoline cut into contact with at least one catalyst the active phase of which comprises at least one metal from group VIII and at least one metal from group VIB deposited on a support formed from at least one oxide, said catalyst being prepared using a process comprising at least:
i) at least one step for bringing at least said support into contact with at least one solution containing at least one precursor of at least said metal from group VIII and at least one precursor of at least said metal from group VIB;
ii) at least one step for bringing at least said support into contact with at least one organic compound formed from at least one cyclic oligosaccharide composed of at least 6 α-(1,4)-bonded glucopyranose subunits;
iii) at least one calcining step to obtain at least said metal from said group VIII and at least said metal from group VIB in the oxide form; then
iv) at least one sulphurization step such that said active phase is in the sulphide form; the steps i) and ii) possibly being carried out separately, in any order, or simultaneously.

In accordance with the selective hydrogenation process of the invention, said metal from group VIII present in the active phase of the catalyst is preferably nickel and said metal from group VIB present in the active phase is preferably molybdenum. In accordance with the selective hydrogenation process of the invention, said catalyst is preferably prepared in the presence of a cyclodextrin as the organic compound.

Surprisingly, it has been discovered that a sulphide catalyst the active phase of which comprises at least one metal from group VIII, preferably a non-noble metal from group VIII, and at least one metal from group VIB prepared in the presence of at least one organic compound formed from at least one cyclic oligosaccharide composed of at least 6 α-(1,4)-bonded glucopyranose subunits, preferably a cyclodextrin, when used in a process for the selective hydrogenation of a gasoline cut, has improved catalytic performances, especially in terms of catalytic activity and/or in terms of selectivity. In particular, such a catalyst has a substantially improved activity for conversion as regards polyunsaturated compounds, especially diolefins. This results in better stability of said catalyst as regards the formation of polymers generated by the presence of polyunsaturated compounds. Further, the selectivity as regards selective hydrogenation of said polyunsaturated compounds, especially diolefinic compounds, is not affected at all, or may even be slightly improved: said catalyst prepared in the presence of at least one organic compound formed from at least one cyclic oligosaccharide composed of at least 6 α-(1,4)-bonded glucopyranose subunits has, in addition, a substantially improved activity for conversion to polyunsaturated compounds, and a slightly improved selectivity as regards the selective hydrogenation of said polyunsaturated compounds, especially diolefinic compounds, to the detriment of the hydrogenation of mono-olefinic compounds.

In addition to the selective hydrogenation of polyunsaturated compounds, the selective hydrogenation process of the invention also permits the joint transformation of light saturated organic sulphur-containing compounds present in the gasoline cut to be hydrotreated: said compounds are made heavier by contact with the mono-olefinic compounds present in said cut to form sulphur-containing compounds, in particular sulphides, with a higher molecular mass. The sulphur-containing compounds formed by converting said light saturated sulphur-containing compounds into heavier compounds are then readily separated from the hydrogenated gasoline cut which is depleted in sulphur by injecting the effluent from the selective hydrogenation process of the invention into a separation train which results in the production of a first stream formed from said light gasoline cut, hydrogenated and substantially depleted in sulphur, having a good octane number which can be sent directly to the gasoline pool without complementary treatment, and a second stream formed by a heavy gasoline cut which is highly sulphur-enriched due to the presence of said heavier sulphur-containing compounds, said second stream being subsequently treated in a hydrodesulphurization unit in order to obtain a gasoline which can also be sent directly to the gasoline pool.

The selective hydrogenation process of the invention can thus produce a light gasoline with a reduced polyunsaturated compounds content, especially diolefins, and with a reduced quantity of light sulphur-containing compounds, especially mercaptans. After having been separated, the gasoline produced thereby contains less than 1% by weight of polyunsaturated compounds, especially diolefins, and preferably less than 0.5% by weight of diolefins. It has an end point of less than 120° C., preferably less than 100° C. and highly preferably less than 80° C. More than 50% of the light sulphur-containing compounds with a boiling point less than that of thiophene (84° C.) present in the initial gasoline cut to be hydrotreated in accordance with the selective hydrogenation of the invention are converted.

DETAILED DESCRIPTION OF THE INVENTION

The present invention concerns a process for the selective hydrogenation of a gasoline cut containing polyunsaturated hydrocarbons containing at least 2 carbon atoms per molecule and having an end point of 250° C. or less, said cut having a polyunsaturated hydrocarbons content in the range 0.5% to 5% by weight and a sulphur content in the range 200 to 5000 ppm by weight, said process consisting of bringing said gasoline cut into contact with at least one catalyst the active phase of which comprises at least one metal from group VIII and at least one metal from group VIB deposited on a support formed from at least one oxide, said catalyst being prepared using a process comprising at least:
i) at least one step for bringing at least said support into contact with at least one solution containing at least one precursor of at least said metal from group VIII and at least one precursor of at least said metal from group VIB;
ii) at least one step for bringing at least said support into contact with at least one organic compound formed from at least one cyclic oligosaccharide composed of at least 6 α-(1,4)-bonded glucopyranose subunits;
iii) at least one calcining step to obtain at least said metal from said group VIII and at least said metal from group VIB in the oxide form; then
iv) at least one sulphurization step such that said active phase is in the sulphide form; the steps i) and ii) possibly being carried out separately, in any order, or simultaneously.

The gasoline cut treated in the selective hydrogenation process of the invention has an end point of less than 250° C. It contains polyunsaturated hydrocarbons containing at least 2 carbon atoms per molecule, and preferably at least 3 carbon atoms per molecule. Said gasoline cut is selected from gasolines from a cokefaction unit, a visbreaking unit and a fluidized bed catalytic cracking unit (FCC). Preferably, said gasoline cut which is treated in the selective hydrogenation of the invention originates from a fluidized bed catalytic cracking unit. More precisely, said polyunsaturated hydrocarbons present in said gasoline cut treated using the process of the invention are in particular compounds comprising at least one diene function, i.e. at least two double bonds. Preferably, said polyunsaturated hydrocarbons are diolefinic compounds, in particular isoprene, 2,4-butadiene or 1,3-pentadiene. The gasoline cut treated in the selective hydrogenation process of the invention, preferably the gasoline cut originating from a fluidized bed catalytic cracking unit, also contains mono-olefinic compounds, for example 2,3-dimethyl-but-1-ene, 4,4-dimethylcyclopentene, 2-methyl-hept-2-ene, hex-1-ene, aromatic compounds, for example ethylbenzene and ortho-xylene and saturated paraffin and/or naphthene type compounds, for example 2-methylhexane and 1-methylcyclopentane. Said gasoline cut treated in the selective hydrogenation process of the invention, preferably said gasoline cut derived from a fluidized bed catalytic cracking unit, has a sulphur content in the range 200 to 5000 ppm by weight, preferably in the range 500 to 2000 ppm. The sulphur present in said gasoline cut, preferably in said fluidized bed catalytic cracking unit, is in the form of sulphur-containing organic compounds, especially thiophenic compounds, benzothiophenic compounds and light saturated sulphur-containing compounds. Examples of thiophenic compounds are 3-methylthiophene and 3,4-dimethylthiophene. Benzothiophene is the preferred benzothiophenic compound. The light saturated sulphur-containing compounds present in said gasoline cut are selected from mercaptans (non-cyclic sulphur-containing compounds having a S—H bond) and light sulphides (compounds with a R—S—R' group where R and R' are hydrocarbon groups). Mercaptans which are usually encountered in the gasoline cut, in particular in the fluidized bed catalytically cracked gasoline cut treated in the selective hydrogenation of the invention, are ethanethiol and propanethiol. Said mercaptans become concentrated in the light fraction of the gasoline to be hydrogenated and more precisely in the fraction with a boiling point of less than 120° C.

The light sulphides which are the most frequently encountered in the gasoline cut, in particular in the fluidized bed catalytically cracked gasoline cut treated in the selective hydrogenation process of the invention, are dimethylsulphide, methylethylsulphide and diethylsulphide, $CS_2$, COS, thiophane and methylthiophane.

A gasoline cut originating from a fluidized bed catalytic cracking unit advantageously employed to carry out the selective hydrogenation process of the invention has the following composition by weight, for example: 0.5% to 5% by weight of diolefinic compounds, 20% to 50% by weight of mono-olefinic compounds, 30% to 60% by weight of aromatic compounds, 20% to 50% by weight of saturated compounds (paraffins+naphthenes) and 200 ppm to 0.5% by weight of sulphur. The quantity of light saturated mercaptans with a boiling point of less than 84° C. preferably represents less than 300 ppm of said gasoline cut.

The selective hydrogenation process of the invention principally consists of selectively hydrogenating polyunsaturated compounds, principally diolefins, to mono-olefins and of transforming light saturated sulphur-containing compounds, principally mercaptans and light sulphides, into heavier sulphides or mercaptans by reaction with the mono-olefins. The reaction for the selective hydrogenation of polyunsaturated compounds, principally diolefins, is intended to eliminate said compounds present in said gasoline cut by conversion of said polyunsaturated compounds to the corresponding alkenes, avoiding total saturation of said compounds in order to prevent the formation of the corresponding alkanes.

The light saturated sulphur-containing organic compounds which are to be transformed in the process of the invention are principally mercaptans and light sulphides. The principal reaction for the transformation of mercaptans consists of thioetherification of the mono-olefins by the mercaptans. This reaction is illustrated below in the precise case of the addition of propane-2-thiol to pent-2-ene in order to form a propyl-pentylsulphide.

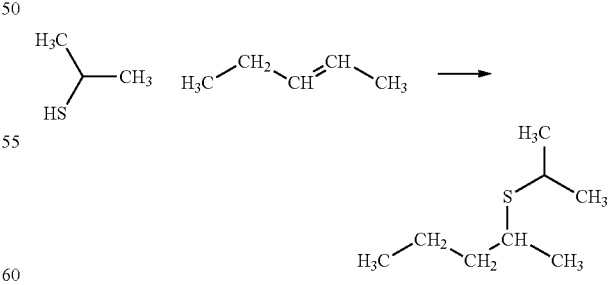

Since the process of the invention is carried out in the presence of hydrogen, the transformation of the sulphur-containing compounds present in the gasoline cut may also occur via the intermediate formation of $H_2S$ which may then add to the unsaturated compounds present in the cut. However, this is a minor pathway under the reaction conditions. The light sulphides which can thus be transformed and made heavier in the process of the invention are principally dimethylsulphide, methylethylsulphide and diethylsulphide, $CS_2$, COS, thiophane and methylthiophane.

The technology of the selective hydrogenation of the invention involves, for example, injecting the gasoline cut and hydrogen into at least one fixed bed, moving bed or ebullated bed reactor, preferably into a fixed bed reactor. The whole of the gasoline cut treated in accordance with the selective hydrogenation process of the invention is preferably injected into the reactor inlet where the selective hydrogenation reaction occurs. However, in some cases it may be advantageous to inject a fraction or all of said gasoline cut between two consecutive catalytic beds placed in said reactor. This implementation can in particular keep the reactor operational even when the reactor inlet is blocked by deposits of polymers, particles or gums present in the gasoline cut.

The selective hydrogenation process of the invention is carried out under the following operating conditions: a temperature in the range 80° C. to 220° C., preferably in the range 90° C. to 200° C., with an hourly space velocity (HSV) in the range 1 h$^{-1}$ to 10 h$^{-1}$ (ratio of volume flow rate of gasoline cut to volume of catalyst loaded into the reactor, in l/l·h), and a total pressure in the range 0.5 MPa to 5 MPa, preferably in the range 1 to 4 MPa. The pressure is adjusted in order that the reaction mixture is mainly in the liquid form in the reactor. The quantity of hydrogen introduced and injected is such that the molar ratio between the hydrogen and the polyunsaturated compounds, preferably diolefins, to be hydrogenated is more than 1 mole/mole and less than 10 mole/mole, preferably in the range 1 to 5 mole/mole.

The catalyst employed to carry out the selective hydrogenation of the invention comprises an active metallic phase deposited on a support, said active phase comprising at least one metal from group VIII of the periodic classification of the elements and at least one metal from group VIB of the periodic classification of the elements. Preferably, said catalyst contains no alkali metals and no alkaline-earth metals.

In general, the quantity of metal(s) from group VIB in said oxide catalyst from said step iii) is in the range 1% to 20% by weight of oxide(s) of metal(s) from group VIB, preferably in the range 5% to 15% by weight of oxide(s) of metal(s) from group VIB. Preferably, the metal from group VIB is molybdenum or tungsten or a mixture of these two elements; more preferably, the metal from group VIB is constituted solely by molybdenum or tungsten. More preferably, the metal from group VIB is molybdenum.

In general, the quantity of metal(s) from group VIII in said oxide catalyst from said step iii) is in the range 1% to 15% by weight of oxide(s) of metal(s) from group VIII, preferably in the range 1% to 10% by weight of oxide(s) of metal(s) from group VIII. Preferably, the metal from group VIII is a non-noble metal from group VIII of the periodic classification of the elements. Highly preferably, the metal from group VIII is selected from nickel, iron, cobalt and a mixture of at least two of these elements. More preferably, said metal from group VIII is constituted solely by cobalt or nickel. Highly preferably, the metal from group VIII is nickel.

The molar ratio of metal(s) from group VIII to metal(s) from group VIB in the oxide catalyst from said step iii) is preferably in the range 1 to 2.5.

Advantageously, the catalyst obtained at the end of said step iv) has a total pore volume measured by mercury porosimetry in the range 0.3 to 1.4 cm$^3$/g, highly preferably in the range 0.4 to 1.4 cm$^3$/g. The mercury porosimetry is measured using ASTM D-4284-92 with a wetting angle of 140°, for example using an Autopore III model apparatus from Micromeritics. The specific surface area of said catalyst is preferably in the range 40 to 300 m$^2$/g, preferably in the range 60 to 280 m$^2$/g.

The support on which the active phase is deposited is advantageously formed from at least one porous solid in the oxide form selected from the group constituted by aluminas, silicas, silica-aluminas or from oxides of titanium or magnesium used alone or as a mixture with alumina or silica-alumina. Highly preferably, the support is essentially constituted by a transition alumina. A "support essentially constituted by a transition alumina" comprises at least 51% by weight, preferably at least 60% by weight and highly preferably at least 80% by weight or even at least 90% by weight of said transition alumina. The term "transition alumina" means, for example, an alpha phase alumina, a delta phase alumina or a gamma phase alumina. Still more preferably, said support is entirely constituted by a transition alumina. Said support formed from at least one oxide has a total pore volume, measured by mercury porosimetry, in the range 0.4 to 1.4 cm$^3$/g and preferably in the range 0.5 to 1.3 cm$^3$/g. The specific surface area of said support is preferably in the range 40 to 350 m$^2$/g, preferably in the range 60 to 300 m$^2$/g. Said porous support is advantageously in the form of beads, extrudates, pellets or irregular, non-spherical agglomerates the specific form of which may be the result of a crushing step. Highly advantageously, said support is in the form of beads or extrudates.

The catalyst employed in the selective hydrogenation process of the invention is prepared using a process comprising at least:

i) at least one step for bringing at least said support into contact with at least one solution containing at least one precursor of at least said metal from group VIII and at least one precursor of at least said metal from group VIB;

ii) at least one step for bringing at least said support into contact with at least one organic compound formed from at least one cyclic oligosaccharide composed of at least 6 α-(1,4)-bonded glucopyranose subunits;

iii) at least one calcining step to obtain at least said metal from said group VIII and at least said metal from group VIB in the oxide form; then iv) at least one sulphurization step such that said active phase is in the sulphide form; the steps i) and ii) possibly being carried out separately, in any order, or simultaneously.

Deposition of at least said metal from group VIII and at least said metal from group VIB on said support in accordance with the implementation of said step i) may be carried out using any method which is well known to the skilled person. Said step i) is preferably carried out by impregnation of the support with at least one solution containing at least one precursor of said metal from group VIII and at least one precursor of said metal from group VIB. In particular, said step i) may be carried out by dry impregnation, by excess impregnation or by deposition-precipitation using methods which are well known to the skilled person. Preferably, said step i) is carried out by dry impregnation, which consists of bringing said catalyst support into contact with a solution containing at least one precursor of said metal from group VIII and at least one precursor of said metal from group VIB, wherein the volume is equal to the pore volume of the support to be impregnated. This solution contains the metallic precursors of the metal or metals from group VIII and of the metal or metals from group VIB in the desired concentration.

Said metal(s) from group VIII and said metal(s) from group VIB are brought into contact with said support using any metallic precursor which is soluble in aqueous phase or organic phase. Preferably, said precursor(s) of the metal(s) from group VIII and said precursor(s) of the metal(s) from group VIB are introduced in aqueous solution. When the metal from group VIII is cobalt, cobalt nitrate, cobalt hydroxide or cobalt carbonate is advantageously used as the precursor. When the metal from group VIII is nickel, nickel nitrate, nickel hydroxide or nickel carbonate is advantageously used as the precursor. When said metal from group VIB is molybdenum, ammonium heptamoybdate or molybdenum oxide is advantageously used. When said metal from group VIB is tungsten, ammonium metatungstate is advantageously used. Any other salt which is known to the skilled person with sufficient solubility in aqueous solution and which can be decomposed during a calcining step, in particular during the calcining step of said step iii), may also be used.

Contact of said organic compound used to carry out said step ii) with said support is carried out by impregnation, in particular by dry impregnation or excess impregnation, preferably by dry impregnation. Said organic compound is preferably impregnated onto said support after dissolving into aqueous solution. The impregnation solution advantageously comprises an acid, for example acetic acid.

Said organic compound is formed from at least one cyclic oligosaccharide composed of at least 6 α-(1,4)-bonded glucopyranose subunits. A spatial representation of a glucopyranose subunit is given below:

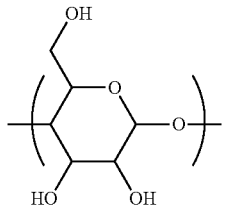

Said organic compound is preferably selected from cyclodextrins, substituted cyclodextrins, polymerized cyclodextrins and mixtures of cyclodextrins. Cyclodextrins are a family of cyclic oligosaccharides composed of α-(1,4)-bonded glucopyranose subunits. They are cage molecules. In accordance with the invention, preferred cyclodextrins are α-cyclodextrin, β-cyclodextrin and γ-cyclodextrin respectively composed of 6, 7 and 8 α-(1,4)-bonded glucopyranose subunits. Developed representations of α-cyclodextrin, β-cyclodextrin and γ-cyclodextrin are given below. Preferably, to carry out said step ii), β-cyclodextrin is used, composed of 7 α-(1,4)-bonded glucopyranose subunits. Cyclodextrins are commercially available compounds.

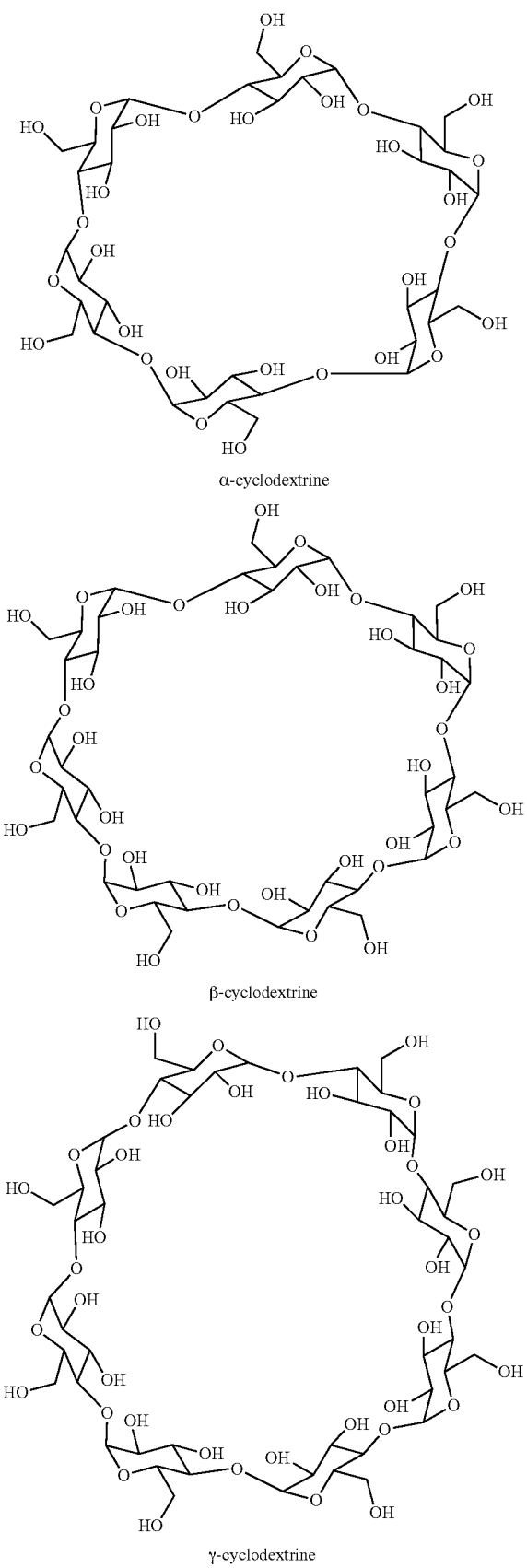 [SMILES: OCC1OC2OC3C(CO)OC(OC4C(CO)OC(OC5C(CO)OC(OC6C(CO)OC(OC7C(CO)OC(OC1C(O)C2O)C(O)C7O)C(O)C6O)C(O)C5O)C(O)C4O)C(O)C3O ; OCC1OC2OC3C(CO)OC(OC4C(CO)OC(OC5C(CO)OC(OC6C(CO)OC(OC7C(CO)OC(OC8C(CO)OC(OC1C(O)C2O)C(O)C8O)C(O)C7O)C(O)C6O)C(O)C5O)C(O)C4O)C(O)C3O ; OCC1OC2OC3C(CO)OC(OC4C(CO)OC(OC5C(CO)OC(OC6C(CO)OC(OC7C(CO)OC(OC8C(CO)OC(OC9C(CO)OC(OC1C(O)C2O)C(O)C9O)C(O)C8O)C(O)C7O)C(O)C6O)C(O)C5O)C(O)C4O)C(O)C3O]

The substituted cyclodextrins advantageously employed to carry out said step ii) are constituted by 6, 7 or 8 α-(1,4)-bonded glucopyranose subunits, wherein at least one is mono- or polysubstituted. The substituents may be attached to one or more hydroxyl group(s) present in the molecule, namely to hydroxyl groups bonded directly to the cycle of a glucopyranose unit and/or to the hydroxyl bonded to the $CH_2$ group itself bonded to the cycle of a glucopyranose unit. More preferably, said substituted cyclodextrins carry one or more substituents, which may be identical or different, selected from saturated or unsaturated alkyl radicals, which may or may not be functionalized, and ester, carbonyl, carboxyl, carboxylate, phosphate, ether, polyether, urea, amide, amine, triazole or ammonium functions. Preferred substituted cyclodextrins are methylated, ethylated, propylated and allyl (i.e. having a function with the semi-developed formula —$CH_2$—CH=$CH_2$) cyclodextrins, succinylated (i.e. having a function with the semi-developed formula R—OCO—$CH_2$—$CH_2$COOH) cyclodextrins, carboxylated, carboxymethylated, acetylated, 2-hydroxypropylated and polyoxyethylenated cyclodextrins. The cyclodextrin mono- or poly-substituent groups may also be a monosaccharide or disaccharide molecule such as a molecule of maltose, glucose, fructose or saccharose.

Particularly advantageous substituted cyclodextrins for carrying out said step ii) are hydroxypropyl beta-cyclodextrin and methylated beta-cyclodextrins.

The polymerized cyclodextrins which are advantageously employed for carrying out said step ii) are polymers wherein the monomers are each constituted by a cyclic oligosaccharide composed of 6, 7 or 8 α-(1,4)-bonded glucopyranose subunits, which may or may not be substituted. A cyclodextrin in the polymerized form, cross-linked or not, which may advantageously be used to carry out said step ii) is, for example, of the type obtained by polymerization of monomers of beta-cyclodextrin with epichlorhydrin or a polyacid.

Advantageous mixtures of cyclodextrins employed in carrying out said step ii) employ substituted or unsubstituted cyclodextrin. Said mixtures could, for example, contain each of the three types of cyclodextrins (alpha, beta and gamma) jointly and in varying proportions.

Introduction of said organic compound, preferably a cyclodextrin and highly preferably beta-cyclodextrin, for carrying out said step ii) is such that the molar ratio {(metal(s) from groups VIII and VIB in the oxide form present in the active phase of the catalyst obtained at the end of said step iii)/organic compound} is in the range 10 to 300, preferably in the range 25 to 180. The metal(s) from groups VIII and VIB taken into account for the calculation of said molar ratio are the metals introduced to carry out said step i) and in the oxide form in the active phase of the catalyst obtained from said step iii). As a result, said metal(s) from group VIII and said metal(s) from group VIB may be in the sulphide form: they will be sulphided prior to carrying out the selective hydrogenation process of the invention.

The process for preparing the catalyst used in the selective hydrogenation process of the invention includes several implementations.

A first implementation consists of carrying out said steps i) and ii) simultaneously such that said organic compound, preferably a cyclodextrin, and at least said precursor of at least said metal from group VIII and at least said precursor of at least said metal from group VIB present in the active phase are co-impregnated onto said support (co-impregnation step). Said first implementation advantageously comprises carrying out one or more steps i). In particular, one or more steps i) advantageously precede and/or follow said co-impregnation step. In accordance with said first implementation, each of the co-impregnation steps carried out is preferably followed immediately by at least one step for maturation then by at least one step for drying then by at least one calcining step. In particular, said co-impregnation step is followed by at least one drying step then by at least one calcining step. Said first implementation may comprise several co-impregnation steps. Said calcining step iii) is at least carried out when all of the steps for depositing at least said metal from group VIII and at least said metal from group VIB onto the catalyst support have been carried out.

A second implementation consists of carrying out said step i) prior to said step ii). In accordance with said second implementation, one or more steps i) for depositing at least said metal from group VIII and at least said metal from group VIB present in the active phase of the catalyst precede(s) said step ii). Preferably, each of said steps i) is followed immediately by a maturation step then by at least one drying step and optionally by at least one calcining step. In particular, the last step i) is advantageously followed by at least one drying step and optionally by at least one calcining step before carrying out said step ii). Said step ii) is advantageously followed by a maturation step then by at least one drying step and highly preferably by at least one calcining step. Said calcining step in accordance with said step iii) is at least carried out either following said step i) after drying or following said step ii) after drying.

A third implementation consists of carrying out said step ii) prior to said step i). Said step ii) is preferably followed immediately by a maturation step then by at least one drying step and optionally by at least one calcining step before carrying out said step i). Advantageously, said step ii) is followed by several steps i). Preparation of the catalyst in accordance with said third implementation is advantageously terminated by said calcining step iii).

Each of the three implementations described above may be carried out independently such that the catalyst used in the process of the invention is prepared either in accordance with said first implementation or in accordance with said second implementation or in accordance with said third implementation. However, it may be advantageous to associate said first implementation with said second implementation or with said third implementation: thus, both the metals from group VIII and from group VIB present in the active phase and the organic compound, preferably a cyclodextrin, are deposited in at least two events on the catalyst support, namely at least once by co-impregnation and at least once by successive impregnation.

Said drying steps carried out to prepare the catalyst prepared in accordance with at least one implementation described above are carried out at a temperature in the range 80° C. to 160° C. They are preferably carried out for a period in the range 1 to 15 hours. Said calcining step iii) is carried out at a temperature in the range 200° C. to 660° C., preferably in the range 300° C. to 550° C. It is preferably carried out for a period in the range 1 to 6 hours. The calcining steps carried out to prepare the catalyst prepared in accordance with at least one implementation described above are advantageously carried out under the same conditions as said step iii).

The catalyst obtained at the end of said step iii) after carrying out steps i) and ii) in accordance with at least one of the three implementations described above is in the oxide state.

The preparation of the catalyst used in the selective hydrogenation process of the invention comprises at least one step iv) for sulphurization such that said active phase is in the sulphide form.

Before being brought into contact with the feed to be treated, the catalysts undergo a sulphurization step. Sulphurization is preferably carried out in a sulpho-reducing medium, i.e. in the presence of $H_2S$ and hydrogen, in order to transform the metallic oxides into sulphides, for example oxides of molybdenum into $MoS_2$ and oxides of nickel into $Ni_3S_2$. Sulphurization is carried out by injecting a stream containing $H_2S$ and hydrogen, or a sulphur-containing compound which can decompose into $H_2S$ in the presence of catalyst and hydrogen, onto the oxide catalyst. The $H_2S$ precursors preferably used to carry out said step iv) are polysulphides such as dimethyldisulphide. The temperature of said sulphurization step is adjusted so that the $H_2S$ reacts with the metallic oxides to form metallic sulphides. Said sulphurization step iv) may be carried out in situ (after loading the catalyst into the reaction unit of the selective hydrogenation process of the invention) or ex situ (before loading the catalyst into the reaction unit of the selective hydrogenation of the invention) at a temperature in the range 200° C. to 600° C. and more preferably in the range 300° C. to 500° C.

Said sulphurization step iv) is carried out such that the metals from group VIII and group VIB are substantially sulphided. An element is considered to be substantially sulphided when the molar ratio between the sulphur (S) present on the catalyst derived from said step iv) and said element is at least equal to 60% (degree of sulphurization of at least 60%) of the theoretical molar ratio corresponding to total sulphurization of the element under consideration:

$$(S/element)_{catalyst} \geq 0.6 \times (S/element)_{theoretical}$$

in which:
$(S/element)_{catalyst}$=molar ratio between sulphur (S) and the element present on the catalyst from said step iv);
$(S/element)_{theoretical}$=molar ratio between the sulphur and the element corresponding to total sulphurization of the element into sulphide.

This theoretical molar ratio varies as a function of the element under consideration:

$(S/Fe)_{theoretical}$=1
$(S/CO)_{theoretical}$=8/9
$(S/Ni)_{theoretical}$=2/3
$(S/Mo)_{theoretical}$=2/1
$(S/W)_{theoretical}$=2/1

The catalyst comprising several metals, the molar ratio between the sulphur present on the catalyst from said step iv) and the series of elements must also be at least equal to 60% of the theoretical molar ratio corresponding to total sulphurization of each element into sulphide, the calculation being carried out pro rata for the relative molar fractions of each element. As an example, for a catalyst comprising molybdenum and nickel with a respective molar fraction of 0.7 and 0.3, the minimum molar ratio (S/Mo+Ni) is given by the relationship:

$$(S/Mo+Ni)_{catalyst}=0.6\times\{(0.7\times2)+(0.3\times(2/3))\}$$

Highly preferably, the degree of sulphurization of the metals is more than 80%.

Before carrying out the selective hydrogenation process of the invention, the catalyst from said step iv) is at least partially in the sulphide form. It may also comprise a metallic oxide phase which has not been transformed during said sulphurization step iv). Said catalyst may be entirely or partially free of said organic compound formed from at least one cyclic oligosaccharide composed of at least 6 α-(1,4)-bonded glucopyranose subunits.

The following examples illustrate the invention without in any way limiting its scope.

EXAMPLES

Catalysts A, B, C and D prepared in Examples 1, 2, 3 and 4 respectively were prepared with the same contents of molybdenum and nickel. The support used for the preparation of each of catalysts A, B, C and D was a gamma alumina with a pore volume of 0.7 ml/g and a BET surface area of 280 $m^2/g$.

Example 1 (Comparative)

Preparation of a Supported Catalyst a (Oxide Catalyst) and a supported catalyst A' (sulphide catalyst) with formula $NiMo/Al_2O_3$ Catalyst A was obtained by dry impregnation of an aqueous solution prepared from ammonium heptamolybdate and nickel nitrate, the volume of the solution containing the molybdenum and nickel precursors being rigorously equal to the pore volume of the alumina support mass. The concentrations of precursors in the aqueous solution were adjusted in order to deposit the desired quantities of Ni and Mo on the alumina support. After a 12 hour maturation step, the solid was dried for 12 hours at 120° C. then calcined in air at 500° C. for 2 hours.

Catalyst A obtained in the oxide state with formulation $NiMo/Al_2O_3$ had a molybdenum content of 7.2 expressed as the % by weight of the oxide $MoO_3$ and a nickel content of 5.6 expressed as the % by weight of the oxide NiO. The Ni/Mo molar ratio of this catalyst A was 1.50.

Catalyst A was sulphurized ex situ at atmospheric pressure in a sulphurization bank in a $H_2S/H_2$ mixture constituted by 15% by volume of $H_2S$ at 1 l/g·h of catalyst, at 400° C. for two hours. A catalyst A' was obtained in the sulphide form (degree of sulphurization more than 60%).

Example 2 (Invention)

Preparation of a Supported Catalyst B (Oxide Catalyst) and a Supported Catalyst B' (Sulphide Catalyst) with Formula $NiMo/Al_2O_3$ in the Presence of β-Cyclodextrin (Co-Impregnation)

Catalyst B was obtained by dry impregnation of an aqueous solution prepared from ammonium heptamolybdate and nickel nitrate, the volume of the solution containing the nickel and molybdenum precursors being rigorously equal to the pore volume of the alumina support mass. The concentrations of precursors in the aqueous solution were adjusted in order to deposit the desired quantities of Ni and Mo on the alumina support. Said aqueous solution also contained β-cyclodextrin (SIGMA-ALDRICH, 98% pure) in a molar ratio (Ni+Mo)/β-cyclodextrin of 30. After a 12 hour maturation step, the solid was dried for 12 hours at 120° C. then calcined in air at 500° C. for 2 hours.

Catalyst B obtained in the oxide state with formulation NiMo had a molybdenum content of 7.1 expressed as the % by weight of the oxide $MoO_3$ and a nickel content of 5.4 expressed as the % by weight of the oxide NiO. The Ni/Mo molar ratio of this catalyst B was 1.47.

Catalyst B was sulphurized ex situ at atmospheric pressure in a sulphurization bank in a $H_2S/H_2$ mixture constituted by 15% by volume of $H_2S$ at 1 l/g·h of catalyst, at 400° C. for two hours. A catalyst B' was obtained in the sulphide form (degree of sulphurization more than 60%).

Example 3 (Invention)

Preparation of a Supported Catalyst C (Oxide Catalyst) and a Supported Catalyst C' (Sulphide Catalyst) with Formula NiMo/Al$_2$O$_3$ in the Presence of β-Cyclodextrin (Co-Impregnation of Ni and Mo then Successive Impregnation of β-Cyclodextrin)

Catalyst C was obtained by dry impregnation of an aqueous solution prepared from ammonium heptamolybdate and nickel nitrate, the volume of the solution containing the nickel and molybdenum precursors being rigorously equal to the pore volume of the alumina support mass. The concentrations of precursors in the aqueous solution were adjusted in order to deposit the desired quantities of Ni and Mo on the alumina support. After a 12 hour maturation step, the solid was dried for 12 hours at 120° C. A second dry impregnation step meant that β-cyclodextrin (SIGMA-ALDRICH, 98% pure) dissolved in water could be added to the dry solid that had been obtained. The (Ni+Mo)/β-cyclodextrin molar ratio was 30. After a 12 hour maturation step, the solid was dried for 12 hours at 120° C. then calcined in air at 500° C. for 2 hours to obtain the catalyst C.

Catalyst C obtained in the oxide state with formulation NiMo had a molybdenum content of 7.0 expressed as the % by weight of the oxide MoO$_3$ and a nickel content of 5.5 expressed as the % by weight of the oxide NiO. The Ni/Mo molar ratio of this catalyst C was 1.50.

Catalyst C was sulphurized ex situ at atmospheric pressure in a sulphurization bank in a H$_2$S/H$_2$ mixture constituted by 15% by volume of H$_2$S at 1 l/g·h of catalyst, at 400° C. for two hours. A catalyst C' was obtained in the sulphide form (degree of sulphurization more than 60%).

Example 4 (not in Accordance)

Preparation of a Supported Catalyst D (Oxide Catalyst) and a Supported Catalyst D' (Sulphide Catalyst) with Formula NiMo/Al$_2$O$_3$ in the Presence of Cellobiose Cellobiose, or β-D-glucopyrannosyl(1→4)D-glucopyrannose, is the product of cellulose degradation. It is a diholoside with empirical formula C$_{12}$H$_{22}$O$_{11}$. It is not a cyclic oligosaccharide. The developed formula of cellobiose is given below:

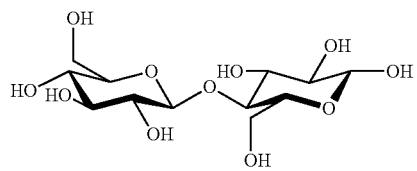

Catalyst D was obtained by dry impregnation of an aqueous solution prepared from ammonium heptamolybdate and nickel nitrate, the volume of the solution containing the nickel and molybdenum precursors being rigorously equal to the pore volume of the alumina support mass. The concentrations of precursors in the aqueous solution were adjusted in order to deposit the desired quantities of Ni and Mo on the alumina support. The solution also contained cellobiose (supplied by WWR) in a (Ni+Mo)/cellobiose molar ratio of 30. After a 12 hour maturation step, the catalyst was dried for 12 hours at 120° C. then calcined in air at 500° C. for 2 hours.

Catalyst D obtained in the oxide state with formulation NiMo had a molybdenum content of 7.1 expressed as the % by weight of the oxide MoO$_3$ and a nickel content of 5.6 expressed as the % by weight of the oxide NiO. The Ni/Mo molar ratio of this catalyst D was 1.52.

Catalyst D was sulphurized ex situ at atmospheric pressure in a sulphurization bank in a H$_2$S/H$_2$ mixture constituted by 15% by volume of H$_2$S at 1 l/g·h of catalyst, at 400° C. for two hours. A catalyst D' was obtained in the sulphide form (degree of sulphurization more than 60%).

Example 5

Catalytic Performances of Catalysts A', B', C' and D' in a Test for the Selective Hydrogenation of a Gasoline Cut Using Model Molecules Representative of a Catalytically Cracked Gasoline A model feed representative of a catalytically cracked gasoline (FCC) containing 1000 ppm by weight of sulphur in the form of 3-methylthiophene, 100 ppm by weight of sulphur in the form of propane-2-thiol (mercaptan), 10% by weight of mono-olefin in the form of hex-1-ene and 1% by weight of diolefins in the form of isoprene in n-heptane was used to evaluate the catalytic performances of the various catalysts.

The selective hydrogenation reaction was operated in a stirred 500 ml autoclave reactor. Each of catalysts A', B', C' and D' was placed in succession in said reactor in contact with 250 ml of said model feed at a total pressure of 1.5 MPa and a temperature of 160° C. The time t=0 of the test corresponded to bringing the catalyst into contact with the feed and hydrogen. The pressure was kept constant during the test by adding hydrogen. The test duration was fixed at 45 minutes and gas chromatographic analysis of the liquid effluents was carried out regularly to evaluate the activities of each of the catalysts for isoprene hydrogenation (selective formation of methylbutenes) and for hex-1-ene hydrogenation (formation of n-hexane). The activity of each catalyst for each of these two hydrogenation reactions is defined as the ratio of the rate constant obtained for each hydrogenation reaction normalized to one gram of catalyst. The rate constant was calculated by assuming first order for the hydrogenation reaction. The activity of each catalyst for each of the two hydrogenation reactions is given by the formula: A(X)=k(X)/m in which A(X)=activity of catalyst for the hydrogenation of compound X in min$^{-1}$/g of catalyst (in sulphide form); k=rate constant for the hydrogenation reaction under consideration, in min$^{-1}$. The constant k is calculated using the formula $$k(X)=(1/45)\times\ln(100/(100-\mathrm{conv}(X)))$$

where 45=duration of test in minutes and conv(X)=conversion of compound X, X being isoprene or hex-1-ene; m=mass of catalyst (sulphide form) engaged in the test.

The selectivity of the catalyst as regards the hydrogenation of isoprene is equal to the ratio of the activities of the catalyst in the hydrogenation of isoprene and of hex-1-ene. It is denoted A(isoprene)/A(hex-1-ene).

The performances of catalysts A', B', C' and D' are given in Table 1.

TABLE 1

Performances of catalysts in model feed selective hydrogenation test

| | Catalyst | | | |
|---|---|---|---|---|
| | A' | B' | C' | D' |
| A(isoprene) × $10^3$ | 22.6 | 29.4 | 31.6 | 23.7 |
| A(isoprene)/A(hex-1-ene) | 98 | 103 | 101 | 97 |

The results shown in Table 1 demonstrate that catalysts B' and C' prepared in the presence of β-cyclodextrin are substantially more active in the hydrogenation of isoprene than catalyst A' prepared in the absence of any organic compounds and than catalyst D' prepared in the presence of cellobiose, which does not belong to the cyclic oligosaccharides family. The results also demonstrate that preparing catalysts in the presence of β-cyclodextrin results in the production of catalysts which are much more active as regards isoprene hydrogenation without affecting the selectivity as regards the hydrogenation of isoprene; in contrast, catalysts B' and C' are slightly more selective than catalysts A' and D' as regards isoprene hydrogenation: catalysts B' and C' thus slightly favour the selective hydrogenation of isoprene to methylbutenes to the detriment of the hydrogenation of hex-1-ene to hexane.

Further, the chromatographic analyses proved that the conversion of the mercaptans present in the form of propane-2-thiol was rapid and complete for all of catalysts A', B', C' and D'.

The invention claimed is:

1. A process for the selective hydrogenation of a gasoline cut containing hydrocarbons having at least 2 double bonds and containing at least 2 carbon atoms per molecule and having an end point of 250° C. or less, said cut having a fraction of hydrocarbons with at least two double bonds in the range of 0.5% to 5% by weight and a sulphur content in the range of 200 to 5000 ppm by weight, said process consisting of bringing said gasoline cut into contact with that least one catalyst the active phase of which comprises at least one metal from group VIII and at least one metal from group VIB deposited on a support formed from at least one oxide, said catalyst being prepared using a process comprising at least:
   i) at least one step for bringing at least said support into contact with at least one solution containing at least one precursor of at least said metal from group VIII and at least one precursor of at least said metal from group VIB;
   ii) at least one step for bringing at least said support into contact with at least one organic compound formed from at least one cyclic oligosaccharide composed of at least 6 α-(1,4)-bonded glucopyranose subunits;
   iii) at least one calcining step to obtain at least said metal from said group VIII and at least said metal from group VIB in the oxide form; then
   iv) at least one sulphurization step such that said active phase is in the sulphide form; the steps i) and ii) possibly being carried out separately, in any order, or simultaneously.

2. A selective hydrogenation process according to claim 1, in which said gasoline cut contains hydrocarbons having at least 2 double bonds and at least 3 carbon atoms per molecule.

3. A selective hydrogenation process according to claim 1, in which said gasoline cut derives from a fluidized bed catalytic cracking unit.

4. A selective hydrogenation process according to claim 1, in which the sulphur present in said gasoline cut is in the form of thiophenic compounds, benzothiophenic compounds, mercaptans, thioethers, $CS_2$, and COS.

5. A selective hydrogenation process according to claim 1, in which the metal from group VIB is molybdenum or tungsten or a mixture of said two elements.

6. A selective hydrogenation process according to claim 1, in which the metal from group VIII is selected from nickel, iron, cobalt and a mixture of at least two of said elements.

7. A selective hydrogenation process according to claim 1, in which the support is essentially constituted by a transition alumina.

8. A selective hydrogenation process according to claim 1, in which said organic compound is selected from cyclodextrins, substituted cyclodextrins, polymerized cyclodextrins and mixtures of cyclodextrins.

9. A selective hydrogenation process according to claim 8, in which the cyclodextrins are α-cyclodextrin, β-cyclodextrin and γ-cyclodextrin respectively composed of 6, 7 and 8 α-(1,4)-bonded glucopyranose subunits.

10. A selective hydrogenation process according to claim 8, in which the substituted cyclodextrins are hydroxypropyl beta-cyclodextrin and methylated beta-cyclodextrins.

11. A selective hydrogenation process according to claim 1, in which said calcining step iii) is carried out at a temperature in the range 200° C. to 660° C.

12. A selective hydrogenation process according to claim 1, carried out under the following operating conditions: a temperature in the range of 80° C. to 220° C., with an hourly space velocity (HSV) in the range of 1 $h^{-1}$ to 10 $h^{-1}$, a total pressure in the range of 0.5 MPa to 5 MPa, and a quantity of hydrogen introduced and injected such that the molar ratio between the hydrogen and the hydrocarbons having at least 2 double bonds to be hydrogenated is more than 1 mole/mole and less than 10 mole/mole.

* * * * *